US009649630B2

(12) United States Patent
Wilson

(10) Patent No.: US 9,649,630 B2
(45) Date of Patent: May 16, 2017

(54) PATCH AREA CELL ADHESION

(71) Applicant: Sophion Bioscience A/S, Ballerup (DK)

(72) Inventor: Sandra Wilson, Birkerød (DK)

(73) Assignee: Sophion Bioscience A/S, Ballerup (DK)

( * ) Notice: Subject to any disclaimer, the term of this patent is extended or adjusted under 35 U.S.C. 154(b) by 240 days.

(21) Appl. No.: 14/371,005

(22) PCT Filed: Jan. 8, 2013

(86) PCT No.: PCT/EP2013/050193
§ 371 (c)(1),
(2) Date: Jul. 8, 2014

(87) PCT Pub. No.: WO2013/104608
PCT Pub. Date: Jul. 18, 2013

(65) Prior Publication Data
US 2014/0353171 A1    Dec. 4, 2014

Related U.S. Application Data

(60) Provisional application No. 61/584,427, filed on Jan. 9, 2012.

(30) Foreign Application Priority Data

Jan. 9, 2012 (EP) .................................. 12150459

(51) Int. Cl.
*B01L 3/00* (2006.01)
*G01N 33/487* (2006.01)
(Continued)

(52) U.S. Cl.
CPC ....... *B01L 3/502715* (2013.01); *B01L 3/5088* (2013.01); *G01N 27/327* (2013.01);
(Continued)

(58) Field of Classification Search
None
See application file for complete search history.

(56) References Cited

U.S. PATENT DOCUMENTS

2002/0110847 A1    8/2002  Baumann et al.
2003/0052002 A1*   3/2003  Vogel ............... G01N 33/48728
                                                        204/403.01
(Continued)

FOREIGN PATENT DOCUMENTS

CA    2316966    6/1999
EP    1221046    2/2006
(Continued)

OTHER PUBLICATIONS

Pfleging, W. et al, "Patterning of polystyrene by UV-Laser radiation for the fabrication of devices for patch clamping", XP40433718A, Proc. of SPIE, vol. 6880 and 68800D, Germany, (2008).
(Continued)

*Primary Examiner* — Jennifer Wecker
(74) *Attorney, Agent, or Firm* — McHale & Slavin, P.A.

(57) ABSTRACT

The invention provides a chip for use in a microfluidic analysis system, for example a patch-clamp system, said chip having improved cell adhesion through a predetermined pattern of hydrophobic and hydrophilic regions. A method for manufacture of the chips, and a method for improving the adhesion of a cell to a chip are also disclosed.

11 Claims, 5 Drawing Sheets

(51) Int. Cl.
*G01N 27/327* (2006.01)
*C12M 1/34* (2006.01)

(52) U.S. Cl.
CPC ...... *G01N 33/48728* (2013.01); *B01L 3/5027* (2013.01); *B01L 2200/0668* (2013.01); *B01L 2200/12* (2013.01); *B01L 2300/0829* (2013.01); *B01L 2300/0861* (2013.01); *B01L 2300/0893* (2013.01); *B01L 2300/161* (2013.01); *B01L 2300/165* (2013.01)

(56) References Cited

U.S. PATENT DOCUMENTS

| | | |
|---|---|---|
| 2004/0146849 A1 | 7/2004 | Huang et al. |
| 2005/0009004 A1* | 1/2005 | Xu .................. G01N 33/48728 435/4 |
| 2005/0279730 A1 | 12/2005 | Miyake et al. |
| 2007/0141231 A1 | 6/2007 | Qiu et al. |
| 2011/0083961 A1 | 4/2011 | Muller et al. |

FOREIGN PATENT DOCUMENTS

| | | |
|---|---|---|
| EP | 2037258 | 12/2013 |
| JP | 2002508516 | 3/2002 |
| JP | 2003511668 | 3/2003 |
| WO | WO0125759 | 4/2001 |
| WO | WO0156771 | 8/2001 |
| WO | WO0216651 | 2/2002 |
| WO | WO2007012991 | 2/2007 |
| WO | WO2009138939 | 11/2009 |
| WO | WO2012004296 | 1/2012 |

OTHER PUBLICATIONS

Hozumi, A. et al, "Oxide Nanoskin formed on Poly(metyl methacrylate)", Langmuir, vol. 19, pp. 7573-7579, (2003).
Wilson, S. et al, "Novel processing for a Polymer Patch Clamping System", IEEE Sensors 2009 Conference, pp. 1538-1541, (2009).
Pfleging, W. et al, "Laser-based Micro and Nanopackaging and assembly II", Proceedings of SPIE, Bellingham, WA, XP040433718, v.6880, figures 7-9, (Jan. 22, 2008).

* cited by examiner

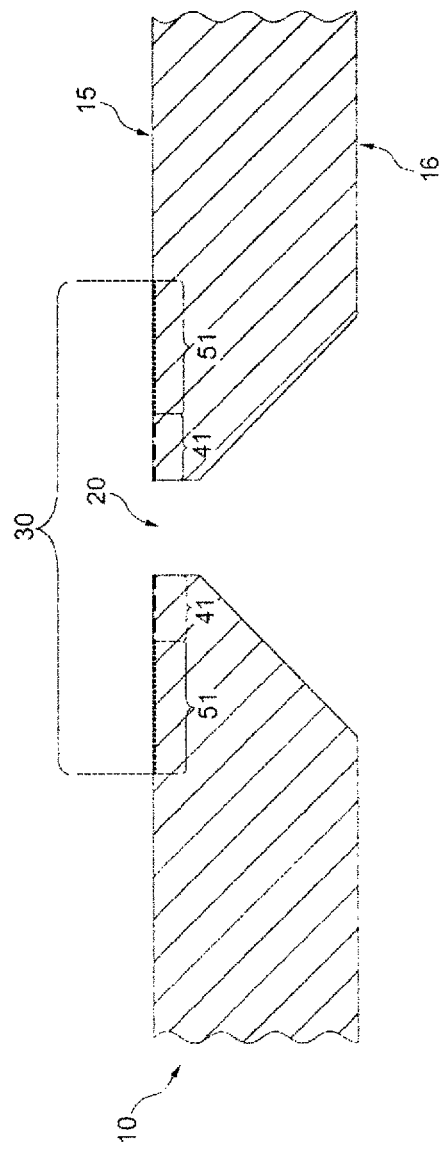

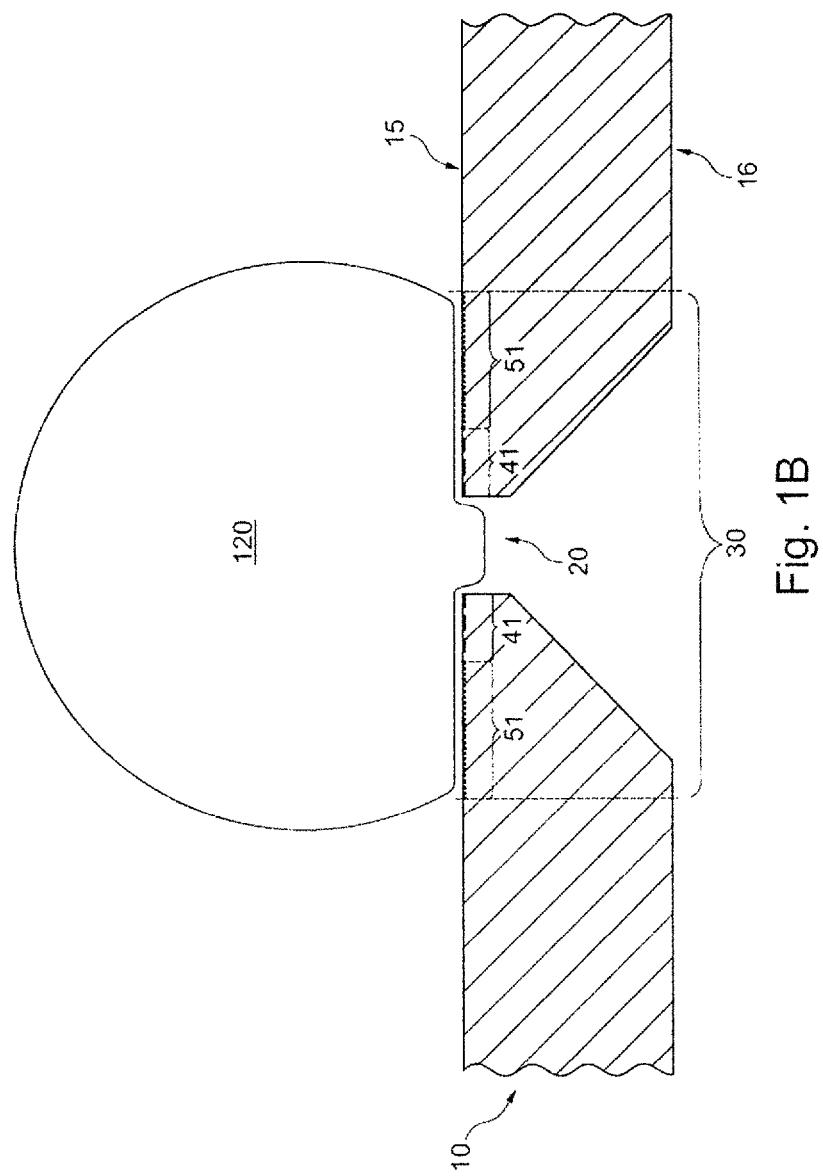

PATCH AREA CELL ADHESION

CROSS REFERENCE TO RELATED APPLICATIONS

This is a national stage filing in accordance with 35 U.S.C. §371 of PCT/EP2013/050193, filed Jan. 8, 2013, which claims the benefit of the priority of European Patent Application No. 12150459.1, filed Jan. 9, 2012, and U.S. Provisional Patent Application No. 61/584,427, filed Jan. 9, 2012, the contents of each are incorporated herein by reference.

FIELD OF THE INVENTION

The present invention relates to a chip for use in a microfluidic analysis system, to the use thereof, and a method of manufacturing such a chip.

The integration of sensor chips in carrier plates, also referred to as microtitre plates, is of particular concern of the present invention. Embodiments of the chip may provide a so-called lab-on-a-chip device, which integrates laboratory functions onto a single chip. An assembly of such chips, which may comprise an array of a plurality of chips on a single carrier, is applicable in a method for determining and/or monitoring electrophysiological properties of ion channels in ion channel-containing structures, typically lipid membrane-containing structures such as cells, by establishing an electrophysiological measuring configuration in which a cell membrane forms a high resistive seal around a measuring electrode, making it possible to determine and monitor a current flow through the cell membrane. The chip is for example useful in a method for analysing the electrophysiological properties of a cell membrane comprising a glycocalyx. The chip may be used in or form part of an apparatus for studying electrical events in cell membranes, such as an apparatus for carrying out patch clamp techniques utilised to study ion transfer channels in biological membranes.

BACKGROUND OF THE INVENTION

Microfluidic analyses of biological systems are widely used in medical and biological research in order to assess the mutual effects of various combinations of reagents and samples. So-called microtitre plates have been developed, which are flat plates with a plurality of wells used as small reactor chambers. Such microtitre plates have become a standard tool in analytical research and clinical diagnostic testing laboratories.

In particular, with chips to be used in patch clamp techniques, good adhesion of the cell to the chip is required, so that a high-resistance seal can be obtained between the chip and the cell membrane (a "gigaseal").

US2002/0110847 describes a method for measuring a state variable of a biological cell.

S. Wilson et al. *IEEE Sensors* 2009 *Conference*, 1538-1541 describes novel processing for a patch clamp system.

Other microfluidic systems are described in US2011/0083961, EP 2 037 258, US 2004/0146849, WO01/56771, WO02/16651 and US2005/0279730.

Despite efforts to date, the need remains for a chip having improved cell adhesion characteristics, which can be manufactured in a simple, effective manner.

OBJECT OF THE INVENTION

It is an object of the invention to provide a chip for use in a microfluidic analysis system, said chip having improved cell adhesion. A method for manufacture of the chips, and a method for improving the adhesion of a cell to a chip are also disclosed.

SUMMARY OF THE INVENTION

It has been found by the present inventors that by providing a specific arrangement of hydrophobic and hydrophilic surfaces around the aperture of a patch clamp chip, cell adhesion is improved.

Accordingly, the present invention relates to a chip for use in a microfluidic analysis system, such as a patch-clamp system. The chip has an upper surface and a central aperture located in said upper surface. The upper surface comprises a cell adhesion region surrounding the aperture. The cell adhesion region comprises two or more alternating hydrophilic and hydrophobic regions. A first hydrophilic region immediately surrounds said aperture and a first hydrophobic region is located radially outwards of, and surrounds, said first hydrophilic region.

The invention also provides a method for improving the adhesion of a cell to a chip. The method comprises the steps of:
a. providing a chip according to the invention;
b. allowing said cell to make contact with the cell adhesion region of said chip, such that the entirety of said cell adhesion region is in contact with said cell, thereby providing improved adhesion of said cell to said chip.

Additionally, a method for the manufacture of a chip according to the invention is provided. The method comprising the steps of:
a. providing a chip precursor having an upper surface, said upper surface comprising a cell adhesion region and said upper surface being hydrophobic in at least said cell adhesion region;
b. creating an aperture in said hydrophobic upper surface, located within said cell adhesion region;
c. modifying the upper surface in a portion of the cell adhesion region, in at least one region immediately surrounding the aperture, so as to provide a first hydrophilic region;
d. optionally, modifying the upper surface in a portion of the cell adhesion region, in at least one other region located radially outwards of, and surrounding said first hydrophilic region, so as to provide a first hydrophobic region.

Further aspects of the invention are set out in the following description text, the enclosed Figures and the dependent claims.

LEGENDS TO THE FIGURES

The invention will now be described with reference to the appended schematic figures, in which:

FIGS. 1A and 1B are a cross-sectional views of a patch clamp device, with (1B) and without (1A) a cell in position.

DETAILED DISCLOSURE OF THE INVENTION

Definitions

Figure 2C:
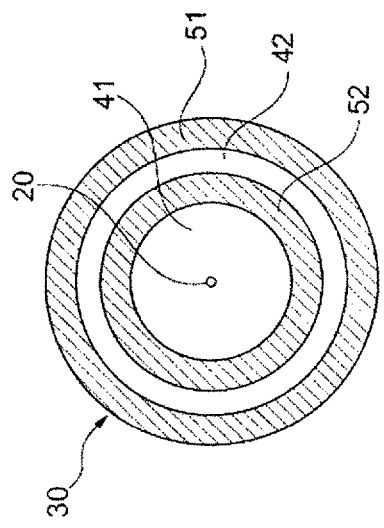
FIGS. 2A-2D illustrate alternative arrangements of hydrophilic and hydrophobic regions

When a first element "surrounds" a second element in a given plane, it means that the first element extends completely about the entirety of the second element, without overlap and without interruption of either element. If a first element "immediately surrounds" a second element in a given plane, this means that there is no intervening region between said first and second elements—i.e. the first element is in contact with the second element about the entire periphery of the second element.

The term "radial" defines a direction in the plane of the surface which is perpendicular to a line passing through the centre of the aperture in said surface. "Radially outwards" is a direction away from the aperture in the plane of the surface, while "radially inwards" is a direction towards the aperture in the plane of the surface.

A material or surface is described as hydrophilic if it has a natural affinity to water. Hydrophilic polymers are defined as those which have a contact angle with water of less than 90°, preferably less than 80°, more preferably less than 75°, even more preferably less than 50° and most preferably less than 20°, measured with an advancing contact angle measurement, as described herein. Conversely, a material or surface is described as hydrophobic if it has a natural aversion to water. Hydrophobic polymers are defined as those which have a contact angle with water of more than 90°, preferably more than 120°, more preferably more than 135°, most preferably more than 150°.

Specific Embodiments of the Invention

FIG. 1 shows a cross-sectional view of a chip 10 according to the present invention, being a patch-clamp device, in which a cell 120 is located on the chip 10.

The chip 10 has substantially planar upper and lower surfaces 15, 16, and a thickness of between 5 and 50 µm. Due to the thin nature of the chip 10, it is also called a "foil".

The material of the chip 10 must be biocompatible, with a high dielectric constant low dielectric loss. The materials should be formable to a high surface finish (average surface roughness, $R_a$<0.5 mm) and be capable of having apertures (through-holes) formed therein in an accurate, reproducible manner, similar to a glass pipette. The chip material should preferably be optically translucent, so that optical analysis techniques such as fluorescence can be carried out.

Suitable materials for the chip 10 include silicon, polymers, pure silica and other glasses such as quartz and pyrex or silica, optionally doped with one or more dopants selected from the group of Be, Mg, Ca, B, Al, Ga, Ge, N, P, As. Polymers are preferred materials for the chip 10. Examples of polymers which are suitable are hydrophobic polymers such as polystyrene, polyimide, polypropylene and polyethylene. Liquid crystal polymers (LCP) are also useful polymers. Polystyrene is the most preferred material for the chip 10.

The upper surface 15 of the chip 10 is preferably substantially planar. This upper surface 15 is configured to support a test item, e.g. an ion-channel containing structure, such as lipid membrane-containing structure, such as a cell, for electrochemical analysis thereof. The electrochemical analysis may hence take place while the test item is subjected to a fluid in contact with the item. It will accordingly be understood that the chip may be capable of conducting an electric current and/or capable of allowing ions to pass there through, e.g. through an orifice or aperture formed therein, so that an electrical connection may be established between two domains on either side of the chip 10.

The chip 10 has a central aperture 20 located in the upper surface 15. As shown in FIG. 1, the aperture 20 is a through-hole which provides a passage from the upper 15 to the lower 16 surface of the chip 10.

The aperture 20 suitably has a circular cross-section, although other cross-sections are possible. The diameter of the aperture 20 at the upper surface is suitably 1-3 µm. The aperture 20 is preferably tapered, such that its diameter at the lower surface 16 is larger than its diameter at the upper surface 15. For instance, the diameter of the aperture 20 at the lower surface is suitably between 1.5 and 10 µm.

Any suitable method for forming the aperture 20 in the chip 10 may be used, depending on the material of the chip 10. The preferred method is excimer laser drilling using short pulse laser radiation (4 nm).

Suction may be applied through the aperture 20 to secure the cell 120 in place over the chip 10 (as per FIG. 1A). Electrodes (not shown) may be provided in both of the aforementioned domains in order to determine an electrical resistance, a flow of ions or a voltage difference across the cell 120 and through the aperture 20.

The upper surface 15 of the chip comprises a cell adhesion region 30 surrounding said aperture 20. The cell adhesion region 30 is the region of the upper surface 15 which is occupied by a single cell 120. Typically, the cell adhesion region is circular, with a radius of between 2 and 25 micrometers, preferably between 5 and 15 micrometers, suitably less than 10 micrometers.

The cell adhesion region 30 comprises at least one hydrophilic region 41, 42 and at least one hydrophobic region 51, 52. FIG. 2A-2D show possible arrangements of the hydrophilic and hydrophobic regions about the aperture 20.

The first hydrophilic region 41 immediately surrounds said aperture 20 and the first hydrophobic region 51 is located radially outwards of, and surrounds, said first hydrophilic region 41. As such, the cell 120, when adhered to the chip 10 makes contact with both hydrophilic and hydrophobic regions.

Suitably, the outermost periphery of said cell adhesion region 30 consists of said first hydrophobic region 51. That is, the first hydrophobic region defines the outermost periphery of the cell adhesion region 30.

Figure 2D:
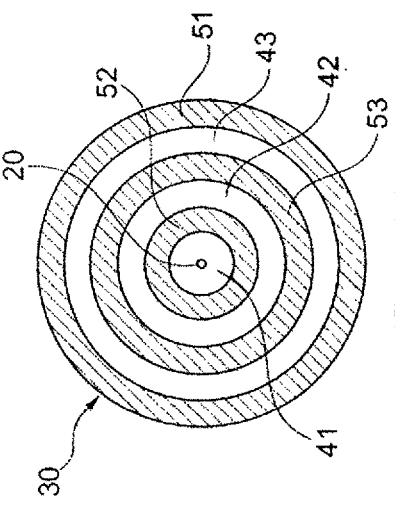
Figure 2A:
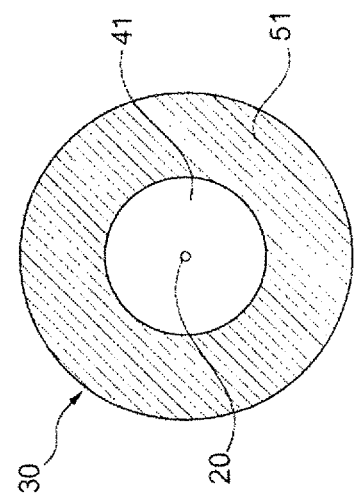
Figure 2B:
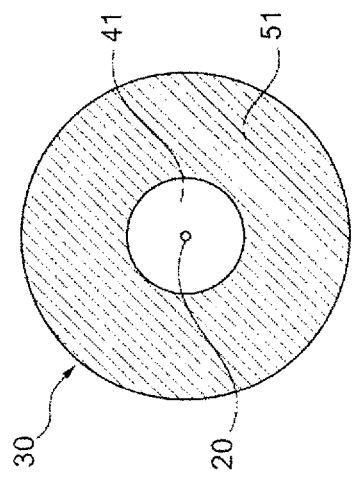
Figure 3:
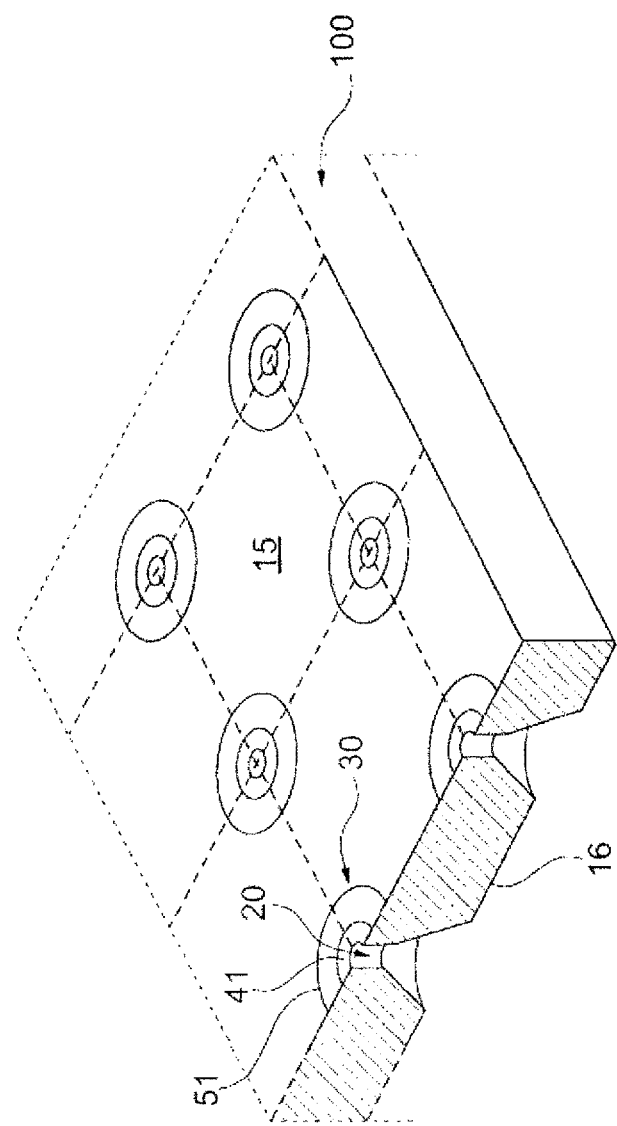
FIG. 3 illustrates a chip assembly according to the invention, in partial cut-away view.

The cell adhesion region 30 comprises two or more, such as three, four, five or six, alternating hydrophilic regions 41, 42, 43 . . . and hydrophobic regions 51, 52, 53 . . . arranged concentrically about the aperture 20 (e.g. FIGS. 2C and 2D).

Suitably, the cell adhesion region 30 consists of at least one hydrophilic region 41, 42 and at least one hydrophobic region 51, 52. In other words, no other regions are present.

The hydrophilic regions may have a total surface area which is at least 50% (50% in FIG. 2A), preferably at least 75% (75% in FIG. 2B) of the surface area of said cell adhesion region 30.

It has been discovered that the ratio of C—O bonds to C=O bonds in the hydrophilic region is also important. Suitably, therefore, the hydrophilic region(s) 41, 42 have a ratio of C—O bonds to C=O bonds of between 0.8:1-1:2.0, preferably 0.9:1-1:1.5, more preferably 1:1. This ratio is measured by X-ray Photon Spectroscopy (XPS), as set out below.

In one aspect, hydrophilic regions 41, 42 are created by surface modification of selected regions of the upper surface 15 within said cell adhesion region 30. Surface modification reduces the need for chip construction using separate materials. Most suitably, hydrophilic regions 41, 42 are created by surface modification of selected regions of the upper surface 15 when the material of the chip 10 is hydrophobic, thus readily creating hydrophobic and hydrophilic regions as required.

The first hydrophilic region 41 surrounds the aperture 20, and may also extend into the aperture 20. Cell adhesion within the aperture and/or encroachment of the cell 120 into the aperture is thus improved.

It has previously been thought that a simple change in the surface structure of the chip (e.g. from hydrophobic to hydrophilic) across the entire cell adhesion region would provide improved cell adhesion. However, the present invention provides improved cell adhesion by varying the hydrophilicity/hydrophobicity of the upper surface 15 within the cell adhesion region according to a predetermined pattern. As such, a single cell 120 occupying the cell adhesion region 30 will make contact with both hydrophilic and hydrophobic regions in a given pattern.

The chip 10 according to the present invention is applicable in: patch clamp analysis; other kinds of electrochemical analyses, in which a wet domain is separated from a dry domain; a coulter counter; flow cytometry; microfluidic analysis systems, wherein electrodes are provided on a single side of the chip 10, e.g. for the purpose of performing measurements on an immobilized or moving cell; miniature cantilever analysis for mass determination of e.g. single cells.

One surface of the chip may, for example, comprise one or more components, which communicate with other components and/or with electronics on the other surface of the chip. For example, an electrical or a fluid passage through the chip may communicate with one or more electrodes and/or measuring components at the first surface of the chip. In such embodiment, the assembly according to the invention is useful as a measuring unit for measuring e.g. pressure, or as a cantilever mass sensor.

The chip 10 of the invention may form part of a chip assembly 100, in which an array of chips 10 are located in a side-by-side arrangement. Suitably, the material of the chip assembly 100 is the same as each individual chip 10 and is continuous between adjacent chips, so that the chip assembly consists of a plate of material with a plurality of apertures 20 and cell adhesion regions 30 located therein. As an alternative, the chips 10 of the present invention are assembled in a carrier structure as per co-pending application PCT/EP2011/061388.

The surface of the chip assembly 100 is suitably recessed in the cell adhesion regions 30, so that a plurality of wells is formed in the chip assembly 100. Typically, a chip assembly 100 consists of 8-400 chips 10.

The invention also relates to a method for improving the adhesion of a cell 120 to a chip 10, said method comprising the steps of:

a. providing a chip 10 according to the invention;
b. allowing said cell to make contact with the cell adhesion region 30 of said chip 10, such that the entirety of said cell adhesion region 30 is in contact with said cell, thereby providing improved adhesion of said cell to said chip 10.

The chip 10 according to the invention may be manufactured via a number of methods. However, a preferred method comprises the steps of:

a. providing a chip precursor 11 having an upper surface 15, said upper surface 15 comprising a cell adhesion region 30 and said upper surface 15 being hydrophobic in at least said cell adhesion region 30;
b. creating an aperture 20 in said hydrophobic upper surface 15, located within said cell adhesion region 30;
c. modifying the upper surface 15 in a portion of the cell adhesion region, in at least one region immediately surrounding the aperture 20, so as to provide a first hydrophilic region 41;
d. optionally, modifying the upper surface 15 in a portion of the cell adhesion region 30, in at least one other region located radially outwards of, and surrounding said first hydrophilic region 41, so as to provide a first hydrophobic region 51.

Principles of Laser Ablation (to Produce Apertures)

An aperture or hole is created by many 'applied shots' of laser energy known as pulses. The depth over which the laser energy is absorbed and therefore, the amount of material removed by a single laser pulse depends on the material's optical properties and the wavelength of the laser.

Basic requirements must be met to structure polymers, such as a sufficient coefficient of absorption ($\alpha_{eff} > 1$ μm$^{-1}$) for the laser wavelength used (Cleve et al., 1999)

In order to drill holes into polymers, the ablation rate R, must be increased above an ablation threshold $\in_\downarrow 1$, which is logarithmic to the energy fluence, $\in$ (Beers Law)

$$R = \frac{1}{\alpha} \ln\left(\frac{\varepsilon}{\varepsilon_1}\right)$$

Very high energy densities and a fast dissolution of ablated fragments leads to a material vapour plasma. This plasma partially absorbs the laser radiation. This is the so-called saturation area (Pettit and Sauerbrey, 1993).

In a laser setup at 193 nm for hole ablation, a laser source and mirrors reflect the light beam through a motorized quartz chrome mask (as used in traditional semi-conductor microlithography), through deflecting mirrors through an objective onto a positioning table where the sample part is placed. The exposure area is approx. 2×2 mm.

In terms of the influence of laser wavelength, a photochemical process happens at wavelengths <200 nm as covalent bonds are broken and material is ablated if energy applied is above the ablation threshold. Volatile fragments are then dissolved. The photon energy for 193 nm is 6.4 eV. It is above the bond energy for most covalent bonds (Laurens, 2000).

At wavelengths >248 nm and depending on material, the electronic excitation does not lead to a break in molecular chains. In this case, rapid heating occurs followed by an explosive evaporation (Pettit and Sauerbrey, 1993). For wavelengths >300 nm single and multiple pulses lead to heating in the energy absorption ranges resulting in a thermal decomposition. A single pulse is insufficient to break covalent bonds (Pettit and Sauerbrey, 1993).

The drilled holes have a diameter on the laser exit side of 1-5 μm to prevent the cell falling through the hole. The diameter of the hole on the laser entrance side should allow electrolyte penetration to the bottom of the cell. Ideally, the hole should be conical. At a fluence of 0.5 mJ/cm$^2$ the best desired result was achieved. The cells sit on the exit side of the hole with a diameter of between 1 and 4 μm. For optimum penetration of cell culture medium, the laser entrance side diameters are between 5-9 μm on average. At laser fluences of 0.8 mJ/cm$^2$ and 1.5 mJ/cm$^2$ the holes are less conical in shape and show an entrance diameter of 5 μm and exit diameter of 3 μm. Increasing the energy fluence shows another behaviour than at 0.5 mJ/cm$^2$. At 0.8 mJ/cm$^2$ the exit diameter is oval and at 1.5 mJ/cm$^2$ the holes are round.

Surface Modification

Suitably, modification of the upper surface 15 in step c. is carried out by irradiation of said upper surface 15, either by UV irradiation or laser irradiation. This can readily be achieved using the same or different lasers as used to create the aperture 20. Photomasking of certain regions of the chip 10 allows selective modification in the desired regions.

Micro-Lithography

Regions of the upper surface 15 may be modified by micro-lithography. Microlithography is the technology used in semiconductor manufacturing to image a pattern from a photomask onto a silicon wafer coated with a UV-light sensitive photoresist material. The photomask has a thin patterned chrome layer on the bottom which is nearly opaque to UV light wavelengths. UV light is passed through the photomask or reflected by the patterned chrome layer. The photoresist on the wafer is then exposed with the shadow pattern of the photomask and a blueprint is created in the resist forming the basic design of, for example, CMOS chips.

There are two basic types of photoresists; positive or negative. When exposed to UV light, the bonds of a positive photoresist such as Clarient AZ4533 are scissioned where subjected to UV light. A salt solution can be used to rinse away broken bond material leaving unexposed photoresist structures behind. In simplified microlithography, a short wavelength lamp at <200 nm preferably at 185 nm can be used to make hydrophilic surface modifications without the need for a photoresist. The photomask is aligned around the drilled hole and the UV light is used with a minimum dose of 1 J/cm$^2$ to break the surface bonds of the polymer material, thus creating stable —COOH bonds.

With a negative photoresist, the reverse occurs. Areas exposed to UV light crosslink and remain on the substrate, while non-crosslinked areas are removed by an organic solvent.

UV Laser Surface Modification

By remaining below the ablation threshold for polystyrene, a patterned surface modification which breaks covalent bonds can be made by using a step and repeat beam process. A laser beam moves across a surface at an energy fluence below the ablation threshold. The ablation threshold is determined experimentally by number of pulses, laser frequency and applied energy. As previously discussed, the 193 nm UV laser has the photonic energy sufficient to break covalent bonds such as in benzene, and ambient air reacts with the broken C—H bonds with the goal of creating more COOH groups. By using a quartz chrome mask in the laser, and some reducing optics, very fine patterns can be 'written' into the surface of the material, and with optimized parameters no dry etching or ablation takes place.

Laser surface modifications can be performed at 193 nm using an ArF ATLEX laser (ATL Laser Technik, Wermelskirchen, Germany) at different energy fluencies, frequencies, and number of pulses and in ambient air. A chromium/quartz mask may also be used but as a projection mask not in contact with the material. The mask feature size demagnification factor to the final achieved feature size is 4:1.

Figure 4:
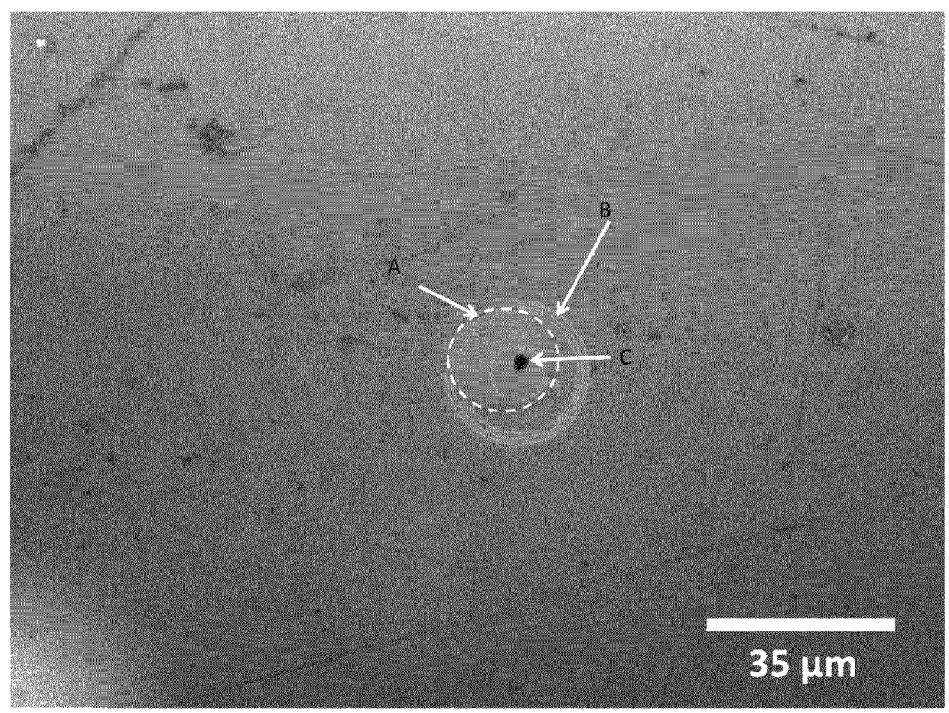
FIG. 4 illustrates the result of laser surface modification of a polystyrene foil to become hydrophilic.

Laser modification is illustrated in FIG. 4. In this example, a foil of polystyrene is provided, the modification is by laser as described above, and then Dip Pen Nano-Lithography (DPNL) lipid rings are applied, The dashed grey circle indicated by (A) is a hydrophilic region. The three concentric rings indicated by (B), and the smaller central ring comprise (DPNL) lipid rings labelled with 5% Rhodamine. Arrow (C) indicates a laser exit hole (2 µm).

As an alternative to irradiation to produce hydrophilic surfaces, modification of the upper surface 15 may be carried out by chemical deposition on the upper surface 15. Such a modification can also provide a hydrophobic region 51. For instance, Hozumi et al. *Langmuir* 2003, 19, 7573-7579 describes the formation of an oxide nanoskin on poly(methylmethacrylate), thus forming hydrophilic regions on the substrate.

In addition to the native material surface hydrophobicity, an additive surface hydrophobicity can be carried out by lithographic processes whereby a layer of hydrophobic material (amorphous glass, amorphous polymer (such as fluoropolymers), semi-crystalline polymer such as polycaprolactone (PCL)) is patterned onto the surface by a lift off technique or by preferential surface affinity.

Dip Pen Nanolithography. In test situations, a Langmuir Blodgett approach to depositing lipids onto hydrophobic surfaces has been attempted with either a single tip or in a multi-tip parallelised approach to produce hydrophobic patterns around a laser drilled. Other methods of applying Langmuir Blodgett types films (such as dipping, spin coating etc) could also be used.

If the upper surface 15 of the chip precursor 11 is sufficiently hydrophobic in the region located radially outwards of, and surrounding said first hydrophilic region 41 (i.e. the first hydrophobic region 51), it can be left without modification. However, it is also possible to coat or otherwise modify this region so as to increase its hydrophobicity to a desired level.

Suitably, the portion of the cell adhesion region 30 which is not the first hydrophilic region 41 constitutes the first hydrophobic region 51.

All modified surfaces are analyzed by XPS and contact angle measurement in addition to cell adhesion.

Contact Angle Measurement Method

An OCA 15 Plus goniometer from DataPhysics (Filderstadt, Germany) with SCA 20 software allows static and dynamic contact angle measurement.

For dynamic contact angle measurement a droplet is placed on the substrate with dosing volume and rate, both variable, and recorded for a specific time by a CCD camera. A contact angle is determined for each individual photo taken. The dynamic contact angle is determined at between 5 and 15 seconds. Distilled water was used for these experiments with a surface energy of 72.8 J/m (with a polar component of 51.1 J/m and a dispersive component of 21.8 J/m) (Gleich, 2004). Due to the interactions of the hydrogen bonds the polar component is larger than the dispersive component.

To measure the advancing contact angle a drop of approx. 2 µL was placed initially on the substrate and the pipette tip was positioned at the centre of the droplet and then water injected at a rate of 0.7 µL/s until a droplet volume of 16 µL was reached. Simultaneously the camera recorded this process with a speed of 16 photos per second for a total of 500 photos over a 20 second duration.

To measure the receding dynamic contact angle the reverse procedure was followed, the pipette tip was positioned in the middle of the droplet and water suctioned up at a rate of 0.7 µL/s, an angle obtained and documented.

Advancing and receding contact angle measurements were performed 5 times for each exposure dose and on different surface locations to ensure an average surface response and prevent already hydrated surfaces being re-measured. The front and back of the foils were measured to determine surface differences due to manufacture or chemistry.

XPS Measurements

X-ray photoelectron spectroscopy (XPS) measurements were carried out on an ESCALAB 5 spectrometer (Vacuum Generators, East Grinsted, UK) using non-monochromatized MgKα radiation (Kα: 1253.6 eV) at a pressure of <10$^{-9}$ mbar. The binding energy scale was referenced to 285.0 eV for the main C1s (C—H bond) feature. The base pressure in the analysis chamber was <10$^{-10}$ mbar and increased to approx. 5×10$^{-8}$ mbar during measurement. The photoelectrons were detected at a take-off angle of 60° with respect to the normal of the sample surface. That means that the informational depth of the measurements is equal to or lower than 5 nm.

Exposed and unexposed reference foil materials are cut into 10×10 mm squares before placement into the measurement chamber. The preparation of SU-8 (a photo-sensitive epoxy resist) surfaces was somewhat more complex. A silicon wafer is laser engraved with a 10×10 mm square matrix for easier sample sectioning after processing. SU-8 is spincoated onto a silicon substrate, soft baked at 95° C. for 2 minutes, then the entire surface is flood exposed under UV light at 365 nm (filtered) with an energy dose of 1000 mJ/cm$^2$, a post-exposure bake of 95° C. for 5 minutes, then developed for 10 minutes in PGMEA, slowly rinsed with isopropanol, and allowed to air dry with the SU-8 layer facing downwards in a fumehood. A short oxygen plasma cleaning step (100 W/5 mins) is performed after sample drying. The samples are separated into 10×10 mm sections using gentle mechanical force before being placed into the measurement chamber.

XPS Results

Surface modifications of polystyrene (PS), polycarbonate (PC) and liquid crystal polymer (LCP, from Rogers Corp., Chandler, Ariz., USA) were carried out using a UV lamp at 185 nm. A quartz glass and chrome mask provided modified and unmodified regions. The lamp was positioned 10 cm from the surface, and treatment was carried out for at least 30 mins, providing 400 milliwatts per cm$^2$.

The surfaces were analyzed using contact angle measurements and XPS to determine the surface chemistry, and roughness was measured using a contact profilometer (Tencor).

Contact angle measurements were performed with an ambient humidity of between 38.8% and 49.4% and temperature ranges between 21.1° and 25°. As these variables are within a narrow range their influences on measurement are considered negligible.

These processing influences can be highlighted particularly clearly using laser ablation. Petri dishes show a ridge type structure if they are structured by UV laser above the ablation threshold. This ridge type structure is considered a material artefact as it cannot be altered by laser radiation density or number of pulses and is also independent of laser direction (parallel or perpendicular to the ridges). For energy fluencies of 20 mJ/cm$^2$, selective material removal occurs in the amorphous areas. Semi-crystalline areas have a higher removal rate leading to ridge-type structures.

A comparison of the effects of different laser pulse widths showed no significant difference in contact angle. Both 20 ns and 4 ns pulse widths only a very small difference was seen in contact angle hysteresis which can be considered negligible.

Chemical analysis using XPS measurements show that for ∈=4 mJ/cm2 the amount of oxygen on PS surfaces increases logarithmically with laser pulse number and total exposure dose. After 150 laser pulses ($E_{tot}$=0.6 J/cm$^2$) and even after 300 laser pulses ($E_{tot}$=1.2 J/cm$^2$) no difference between the used laser pulse lengths could be observed. After 150 laser pulses the amount of oxygen at the surface was 12 at % and after 300 pulses the content of oxygen was 17-18 at %. For both laser pulse lengths and for UV-lamp assisted processing the C1s and O1s line shape of the modified polystyrene surface corresponds very well with the line shape of the chemical group —COOH.

UV-lamp modification also leads to a logarithmic increase in oxygen stoichiometry as a function of exposure time T and total exposure dose $E_{tot}$ (FIG. 50). After long-term exposure (T=90 minutes, $E_{tot}$=1.5 J/cm$^2$) oxygen content reaches a value of about 34 at %. After 4000 laser pulses ($E_{tot}$=16 J/cm$^2$) and with oxygen as processing gas a similar oxygen stoichiometry can be reached. This means that laser modification with 150 or 300 laser pulses leads to a polystyrene surface which is not fully oxidized, this agrees very well with the results which were obtained by contact angle measurements.

The logarithmic increase in oxide layer thickness is typical for physisorption and subsequent chemisorption processes at the surface. The reaction zone is limited to the nanometer-scale and bulk diffusion of oxygen can be neglected.

The XPS measurements provided the following data (Table 1)

|     | C—OH | C=O | Cell attachment |
| --- | --- | --- | --- |
| PS  | 1   | 1   | *** |
| PC  | 1.5 | 1   | *   |
| LCP | 1   | 1   | *** |

Cell attachment was analysed by coating the modified surfaces with cells under a 48 h period, dyeing the cells and visually determining whether cells attached or not. The cell types used were L292 (murine fibroblast cells), HEPG2 (human hepatocellular liver carcinoma cells) and PC-12GFP (rat liver adrenal gland tumour cells).

Three stars (***) indicated good adhesion, while one star (*) indicated poor adhesion. It can be seen that a ratio of C—O bonds to C=O bonds in the hydrophilic regions of around 1:1 provides good cell attachment, which then weakens at a lower ratio.

While the invention has been discussed in relation to a number of specific embodiments and examples, the scope thereof should not be considered as being limited to these embodiments and examples. Instead, the scope of the invention is defined in the appended claims.

The invention claimed is:

1. A chip (10) for use in a microfluidic analysis system, said chip (10) having an upper surface (15) and a central aperture (20) located in said upper surface (15), said upper surface (15) comprising a cell adhesion region (30) surrounding said aperture (20), wherein said cell adhesion region (30) comprises two or more alternating hydrophilic and hydrophobic regions (41, 42, 51, 52) arranged concentrically about said aperture (20), wherein a first hydrophilic region (41) immediately surrounds said aperture (20) and wherein a first hydrophobic region (51) is located radially outwards of, and surrounds, said first hydrophilic region (41); wherein the first hydrophilic region (41) extends into the aperture (20); and wherein hydrophilic regions (41, 42) are created by surface modification of selected regions of the upper surface (15) within said cell adhesion region (30); wherein the first hydrophilic region (41) is formed by irradiation of the upper surface by lamp or laser treatment having a wavelength of <200 nm.

2. A chip (10) according to claim 1, wherein the outermost periphery of said cell adhesion region (30) consists of said first hydrophobic region (51).

3. A chip (10) according to claim 1, wherein the cell adhesion region (30) comprises four, five or six, alternating hydrophilic and hydrophobic regions (41, 42, 51, 52) arranged concentrically about the aperture (20).

4. A chip (10) according to claim 1, wherein the hydrophobic regions have a combined surface area which is at least 50%, preferably at least 75% of the surface area of said cell adhesion region (30).

5. A chip (10) according to claim 1, wherein the cell adhesion region (30) consists of at least one hydrophilic region (41, 42) and at least one hydrophobic region (51, 52).

6. A chip (10) according to claim 1, wherein the cell adhesion region (30) is circular and has a radius of between 2 and 25 micrometers, preferably between 5 and 15 micrometers.

7. A chip (10) according to claim 1, wherein the hydrophilic region(s) (41, 42) have a ratio of C—O bonds to C=O bonds of between 0.8:1-1:2.0, preferably 0.9:1-1:1.5, more preferably 1:1.

8. A chip assembly (100) comprising a plurality of chips (10) according to claim 1.

9. A method for improving the adhesion of a cell to a chip (10), said method comprising the steps of:
  a. providing a chip (10) according to claim 1;
  b. allowing said cell to make contact with the cell adhesion region (30) of said chip (10), such that the entirety of said cell adhesion region (30) is in contact with said cell, thereby providing improved adhesion of said cell to said chip (10).

10. A method for the manufacture of a chip (10) according to claim 1, said method comprising the steps of:
  a. providing a chip precursor (11) having an upper surface (15), said upper surface (15) comprising a cell adhesion region (30) and said upper surface (15) being hydrophobic in at least said cell adhesion region (30);
  b. creating an aperture (20) in said hydrophobic upper surface (15), located within said cell adhesion region (30);
  c. modifying the upper surface (15) in a portion of the cell adhesion region, in at least one region immediately surrounding the aperture (20) and extending into said aperture (20), so as to provide a first hydrophilic region (41); and wherein hydrophilic regions (41, 42) are created by surface modification of selected regions of the upper surface (15) within said cell adhesion region (30); wherein the first hydrophilic region (41) is formed by irradiation of the upper surface by lamp or laser treatment having a wavelength of <200 nm;
  d. optionally, modifying the upper surface (15) in a portion of the cell adhesion region (30), in at least one other region located radially outwards of, and surrounding said first hydrophilic region (41), so as to provide a first hydrophobic region (51).

11. A method according to claim 10, wherein the modification in step c. is carried out by chemical deposition on the upper surface (15).

* * * * *